(12) United States Patent
Shieh et al.

(10) Patent No.: US 9,551,665 B2
(45) Date of Patent: Jan. 24, 2017

(54) METHOD FOR DETECTING MITOCHONDRIA GENE ALTERATIONS

(71) Applicant: NATIONAL CHENG KUNG UNIVERSITY, Tainan (TW)

(72) Inventors: Dar-Bin Shieh, Tainan (TW); Gwo-Bin Lee, Hsinchu (TW); Chen-Min Chang, Hsinchu (TW); Li-Fang Chiu, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 230 days.

(21) Appl. No.: 13/632,510

(22) Filed: Oct. 1, 2012

(65) Prior Publication Data
US 2014/0093871 A1    Apr. 3, 2014

(51) Int. Cl.
*C12Q 1/68* (2006.01)
*G01N 21/64* (2006.01)

(52) U.S. Cl.
CPC ......... *G01N 21/6486* (2013.01); *C12Q 1/6851* (2013.01)

(58) Field of Classification Search
None
See application file for complete search history.

(56) References Cited

U.S. PATENT DOCUMENTS

2010/0196881 A1*  8/2010  Callison et al. ................ 435/6

OTHER PUBLICATIONS

Maricic. PLoS One. 2010. 5(11): e14004.*
Wallace. PNAS. 1994. 91(19): 8739-8746.*
Guttman et al. Clinical Chemistry. 2001. 47(8): 1469-1472.*
Chen-Min Chang, Dar-Bin Shieh, Li-Fang Chiu and Gwo-Bin Lee, The 15th International Conference on Miniaturized Systems for Chemistry and Life Sciences, Oct. 2-6, 2011, Washington State Convention Center 800 Convention Place Seattle, USA.

* cited by examiner

*Primary Examiner* — Joseph G Dauner
(74) *Attorney, Agent, or Firm* — Bacon & Thomas, PLLC

(57) ABSTRACT

The present invention relates to a method for detecting mitochondria alterations, which comprises the following steps: (A) providing a separation element and a sample; (B) mixing the separation element and the sample, wherein a detecting sample is obtained through the binding of a DNA fragment on the separation element to mitochondrial DNA in the sample; (C) dividing the detecting sample into a comparison group and a detection group; (D) adding an amplification solution into the comparison group and the detection group respectively to begin a DNA amplified reaction, and further adding a restriction enzyme into the detection group, wherein the amplification solution comprises a labeling reagent and a primer pair; and (E) detecting amounts of the labeling reagent in the comparison group and the detection group respectively after the DNA amplified reaction.

7 Claims, 9 Drawing Sheets

SEQUENCE LISTING

<160> NUMBER OF SEQ ID NOS: 5

<210> SEQ ID NO 1
<211> LENGTH: 24
<212> TYPE: DNA
<213> ORGANISM: Artificial
<220> FEATURE:
<223> OTHER INFORMATION: synthesized primer

<400> SEQUENCE: 1
tggtattttc gtctgggggg tatg                                          24

<210> SEQ ID NO 2
<211> LENGTH: 18
<212> TYPE: DNA
<213> ORGANISM: Artificial
<220> FEATURE:
<223> OTHER INFORMATION: synthesized primer -continued

```
<400> SEQUENCE: 2
taatccaggt cggtttct                                                    18

<210> SEQ ID NO 3
<211> LENGTH: 18
<212> TYPE: DNA
<213> ORGANISM: Artificial
<220> FEATURE:
<223> OTHER INFORMATION: synthesized primer

<400> SEQUENCE: 3
tatgttgatg cgtttccg                                                    18

<210> SEQ ID NO 4
<211> LENGTH: 20
<212> TYPE: DNA
<213> ORGANISM: Artificial
<220> FEATURE:
<223> OTHER INFORMATION: synthesized primer

<400> SEQUENCE: 4
cactctgcat caactgaacg                                                  20

<210> SEQ ID NO 5
<211> LENGTH: 20
<212> TYPE: DNA
<213> ORGANISM: Artificial
<220> FEATURE:
<223> OTHER INFORMATION: synthesized primer

<400> SEQUENCE: 5
agtccaatgc ttcactcagc                                                  20
```

METHOD FOR DETECTING MITOCHONDRIA GENE ALTERATIONS

BACKGROUND OF THE INVENTION

1. Field of the Invention

The present invention relates to a method for detecting mitochondria gene alterations and, more particularly, to a method for detecting mitochondria gene alterations by means of a single primer pair.

2. Description of Related Art

Mitochondria are the main sites in cells where oxidative phosphorylation occurs and adenosine triphosphate is synthesized, and energy to human and animal cells comes from. Furthermore, mitochondria not only can provide energy, they also work to take part in apoptosis, cellular differentiation and signaling, as well as cell growth and cell cycle. Hence, whether the mitochondria genes are defective or not is instrumental to the functioning of human and animal cells.

Recent studies have found that mitochondria genes can be made susceptible to gene variations, including mutations and deletions, when exposed to attack of free radicals that are generated during oxidation. Such alterations in mitochondria genes can heavily influence biological functions related to mitochondria or can even lead to cell death. An example of known diseases or symptoms incurred by mitochondria gene alterations includes degenerative diseases. Some studies have also suggested that link between mitochondria gene alterations and cancers. Hence, detection for alterations in mitochondria genes would prove to be helpful for diagnosing diseases in clinical practices.

The majority of currently understood methods for detecting mitochondria gene alterations are focused on using direct DNA sequencing; however, the technicality of direct DNA sequencing is complicated and the material and the device required in its operation are expensive, so this technique has not been widely received by testing services and institutions.

In response, it is desirable to provide a rapid and simple device and method for detecting mitochondria gene alterations, which can be applied to clinical uses to examine mitochondria gene related diseases, and from which to use as a reference for treating or diagnosing diseases.

SUMMARY OF THE INVENTION

An object of the present invention is to provide a method for detecting mitochondria gene (mtDNA) alterations, which can not only determine occurrence of mitochondria gene alterations, but also quantify the same.

Another object of the present invention is to provide a device and a system for detecting mtDNA alterations, wherein the device has a three dimensional structure. Hence, extraction and detection processes can be performed on the mitochondria genes in a single device, and making it possible to determine in a rapid and precise fashion whether there are gene alterations in the mitochondria genes. On a particular note, the device and the system of the present invention are the resulting device and system realized from using the present invention's method for detecting mtDNA alterations.

To achieve the above-identified object, the device of the present invention comprises: a purification unit containing a first reaction chamber and a separation-element disposed chamber, wherein the separation-element storage chamber connects to the first reaction chamber through a first pump; and a detection unit disposed under the purification unit, wherein the detection unit comprises: a second reaction chamber and a detecting-sample chamber, the second reaction chamber connects to the first reaction chamber, and the detecting-sample chamber connects to the second reaction chamber through a second pump. Herein, the first reaction chamber and the second reaction chamber connect to each other. More specifically, the first reaction chamber and the second reaction chamber connect to each other to form a reaction chamber.

In the aforementioned device of the present invention, when a sample contained with mitochondria genes is placed into the first reaction chamber, a separation element contained in the separation-element storage chamber can be introduced into the first reaction chamber by the first pump. Then, the separation element is mixed with the sample to perform an extraction process on the mitochondria genes. The first reaction chamber and the second reaction chamber connect to each other, so the sample contained in the reaction chamber can be later introduced into the detecting-sample chamber by the second pump after the extraction process and then a process for detecting mitochondria gene alterations is performed on the sample introduced into the detecting-sample chamber. Then, due to the interconnection between the first reaction chamber and the second reaction chamber, the detecting-sample obtained from the extraction process of the separation unit can be introduced into the detecting-sample chamber through the help of the second pump for carrying out detection for mitochondria genes alterations and the like.

According to the aforementioned device of the present invention, the extraction and detection processes can be performed on the mitochondria genes in a single device. Hence, in contrast to the case with a conventional device that the extraction process has to be performed in conjunction with another extraction device, the whole series of detection steps can be further simplified by using the device of the present invention.

In the device for detecting mtDNA alterations of the present invention, the purification unit may further comprises a washing-solution disposed camber, which connects to the first reaction chamber through a third pump. When the separation element contained in the separation-element storage chamber is mixed with the sample, a washing solution contained in the washing-solution storage chamber can be introduced into the first reaction chamber by the third pump to remove other matrix in cells except for the mitochondria genes. Herein, the washing solution is not particularly limited, and can be any cell-washing solution generally used in the art, such as PBS.

In addition, the device for detecting mtDNA alterations of the present invention may further comprise a micro-mixture unit connecting to the first reaction chamber in order to extract and wash the sample more uniformly.

In one aspect of the device for detecting mtDNA alterations of the present invention, the detection unit may further comprise: a comparison chamber connecting to the second reaction chamber through the second pump. Herein, DNA amplified reactions can be selectively performed on the samples contained in the comparison chamber and the detecting-sample chamber. Then, DNA signals emitted from the comparison chamber are compared with those emitted from the detecting-sample chamber to determine whether the mitochondria genes are alternated or not.

In another aspect of the device for detecting mtDNA alterations of the present invention, the detection unit may further comprise: a mitochondria-gene checking chamber and a temporary chamber, wherein the mitochondria-gene checking chamber and the temporary chamber connect to the second reaction chamber through a fourth pump, and the temporary chamber also connects to the detecting-sample chamber through the second pump. Herein, the DNA amplified reaction can be firstly performed on the sample contained in the mitochondria-gene checking chamber to determine whether the mitochondria genes are extracted by the separation element or not. After the checking process confirmed that the extraction process is successful, the sample contained in the temporary chamber is then introduced into the detecting-sample chamber through the second pump to perform the sequential detection process.

In the aforementioned aspect of the device for detecting mtDNA alterations, the detection unit may further comprise: a comparison sample chamber, which connects to the temporary chamber through the second pump. Hence, the sample contained in the temporary chamber can be introduced into the detecting-sample chamber and the comparison sample chamber by the second pump, and then DNA amplified reactions and other reactions (such as restriction enzyme digestion) can be selectively performed on the samples contained in the detecting-sample chamber and the comparison sample chamber. Finally, the signals emitted from the comparison sample chamber are compared with those emitted from the detecting-sample chamber to determine whether the mitochondria genes are alternated or not.

The devices for detecting mtDNA alterations according to all the aforementioned aspects of the present invention may further comprise plural gas inlets, wherein each gas inlets connects to each elements of the purification unit or the detection unit such as the first pump, the second pump, the third pump, the forth pump, the micro-mixture unit, and the temporary chamber by corresponding connection paths.

In addition, in the devices for detecting mtDNA alterations according to all the aforementioned aspects of the present invention, the first pump, the second pump, the third pump and the forth pump can be any micro-pump generally used in the art such as peristaltic micropumps and suction-type micropumps. Preferably, the first pump and the third pump are peristaltic micropumps respectively, and the second pump and the forth pump are suction-type micropumps respectively.

Furthermore, in the devices for detecting mtDNA alterations according to all the aforementioned aspects of the present invention, all the elements are in micro-sized, so the length, the weight and the height of the whole devices can be confined to several tens of millimeters (mm). Hence, the devices of the present invention can be designed as portable and disposable devices.

Except for the aforementioned devices for detecting mtDNA alterations of the present invention, the present invention further provides a system using the aforementioned devices. The system for detecting mtDNA alterations of the present invention comprises: the aforementioned device for detecting mtDNA alterations; a temperature controller disposed surrounding the periphery of the device to control a temperature of the device; and an analysis device disposed over the device to detect signals emitting from the device.

In the system of the present invention, the temperature controller is used to control the temperature of the device, in order to perform the detection process such as the DNA amplified reaction. Herein, the temperature controller may comprise: a sensing module and a control module. The sensing module can detect the temperature of the device, and then the temperature of the device is increased or decreased by the control module.

In addition, the system for detecting mtDNA alterations of the present invention may further comprise: a heater/cooler device, which is disposed under the device for detecting mtDNA alterations and connects to the temperature controller. The heater/cooler device can change the temperature of the device rapidly. In the present invention, the heater/cooler device is not particularly limited, and can be any heater/cooler device generally used in the art, such as a thermoelectric cooler (TE cooler), a hot plate and a MEMS heater. Preferably, the heater/cooler device used in the present invention is a TE cooler. It is because that the TE cooler can increase and decrease temperature rapidly. In addition, the TE cooler further can increase and decrease temperature in large area, and the temperature range thereof is broad (−10° C. to 200° C.).

Furthermore, in the system for detecting mtDNA alterations of the present invention, the analysis device can be selected according to the DNA signal to be detected. The analysis device used in the present invention can be any analysis device generally used in the art, such as an electrophoresis device, a fluorescence device and a UV-light detecting device. Preferably, the analysis device used in the system of the present invention is a fluorescence device. More preferably, the analysis device used in the system of the present invention is a fluorescence device equipped with a photomultiplier tube (PMT).

When magnetic beads are used to extract the mitochondria genes in the device for detecting mtDNA alterations of the present invention, the system for detecting mtDNA alterations of the present invention may further comprise an electromagnetic controller, which provides a magnetic field to the device for detecting mtDNA alterations. Hence, when the electromagnetic controller provides a magnetic field to the device, the magnetic beads can be absorbed by the magnetic field. In this case, it is unnecessary to perform an additional separation step to obtain the purpose of extracting the mitochondria genes.

Except for the aforementioned device and system for detecting mtDNA alterations, the present invention further provides a method for detecting mtDNA alterations, and this method is particularly suitable for the device and the system of the present invention. However, the method of the present invention is not limited to be applied to the device and the system of the present invention, and it can also be applied to other devices and systems.

The method for detection mtDNA alterations of the present invention comprises the following steps: (A) providing a separation element and a sample contained with mitochondria genes, wherein the separation element is modified with a DNA fragment for recognizing mitochondria genes; (B) mixing the sample and the separation element to separate the mitochondria genes from the sample through a binding between the DNA fragment of the separation element and the mitochondria genes in the sample, and sequentially obtaining a detecting sample contained with the mitochondria genes; (C) dividing the detecting sample into a comparison group and a detection group; (D) adding an amplification solution into both the comparison part and the detection part respectively and further adding a restriction enzyme into the detection group to perform a DNA amplified reaction, wherein the amplification solution comprises a labeling reagent and a primer pair; and (E) detecting amounts of the labeling reagent in the comparison group and the detection group respectively after the DNA amplified reaction, wherein when the amount of the labeling reagent in the comparison part is different from that in the detection group, it indicates that a mtDNA alteration is present in the sample.

It should be noted that the primer pairs added into the comparison group and the detection group are the same primer pairs. Hence, when the method of the present invention is used, the purpose of detecting mtDNA alterations can also be accomplished at the expense of only a single primer pair. However, when the conventional method is used, two primer pairs has to be used, wherein one primer pair is paired with normal sequence of a target gene region, and the other primer pair is paired with mutated sequence of the target gene region. Hence, the method of the present invention is more convenient than the conventional method.

More specifically, in the method of the present invention, when the amount of the labeling reagent in the detection group is less than that in the comparison group, it indicates that a mtDNA alteration is present in the sample.

In addition, the restriction enzyme used in the step (D) can be a restriction enzyme capable of digesting DNAs in a target gene region of the mitochondria genes, and the target gene region can be a mutation region to be detected in the mitochondria genes. Herein, the restriction enzyme is selected according to the sequence of the target gene region in the mitochondria genes, and can be any restriction enzyme generally used in the art.

In the method for detection mtDNA alterations of all aspects of the present invention, the primer pair used in the step (D) is a primer pair to amplify a target gene region of the mitochondria genes. Herein, any DNA amplified reaction such as a polymerase chain reaction (PCR) and a real-time polymerase chain reaction (real-time PCR) can be used in the method of the present invention to amplify the mitochondria genes.

In addition, the labeling reagent used in the step (D) can be a dye detected with fluorescence or UV-light. Preferably, the labeling reagent is a fluorescent dye. More preferably, the labeling reagent is a fluorescent dye such as SybrGreen that can emit fluorescence when it chelates into major grooves of DNAs.

The methods for detection mtDNA alterations of all aspects of the present invention may further comprise a step (B') after the step (B): dividing the detecting sample into a mitochondria gene-checking group and a detecting sample group, and detecting whether the mitochondria genes are present in the mitochondria gene-checking group or not. In this case, the step (C) is: dividing the detecting sample group into a comparison group and a detection group. Only when it is confirmed that the mitochondria genes are present in the mitochondria gene-checking group, the sequential steps (C) and (D) are performed. In the step (B'), any conventional method generally used in the art such as a PCR and a real-time PCR can be used to check whether the mitochondria genes are present in the mitochondria gene-checking group or not. When the PCR or the real-time PCR are used to check the mitochondria genes in the mitochondria gene-checking group, the used primer pair is not particularly limited, as long as it can amplify the mitochondria gene. Preferably, the used primer pair can pair with a D-loop region of the mitochondria genes.

In the method for detecting mtDNA alterations of all aspects of the present invention, the separation element used in the step (A) can be any separation element generally used in the art, such as a magnetic bead or a polymer bead. When the magnetic bead is used as the separation element, the mitochondria genes can be extracted with a magnetic field. When the polymer bead is used as the separation unit, the extraction of the mitochondria gene can be accomplished by gravitational or centrifugal force.

DETAILED DESCRIPTION OF THE PREFERRED EMBODIMENT

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

In the following embodiments of the present invention, the figures are simplified perspective views. However, only the elements relate to the present invention are shown in these figures. These shown embodiments are not actual performance aspects. The numbers, the shapes and the sizes of the shown elements are only one selective design, and they may be more complicated.

Embodiment 1

Figure 1:
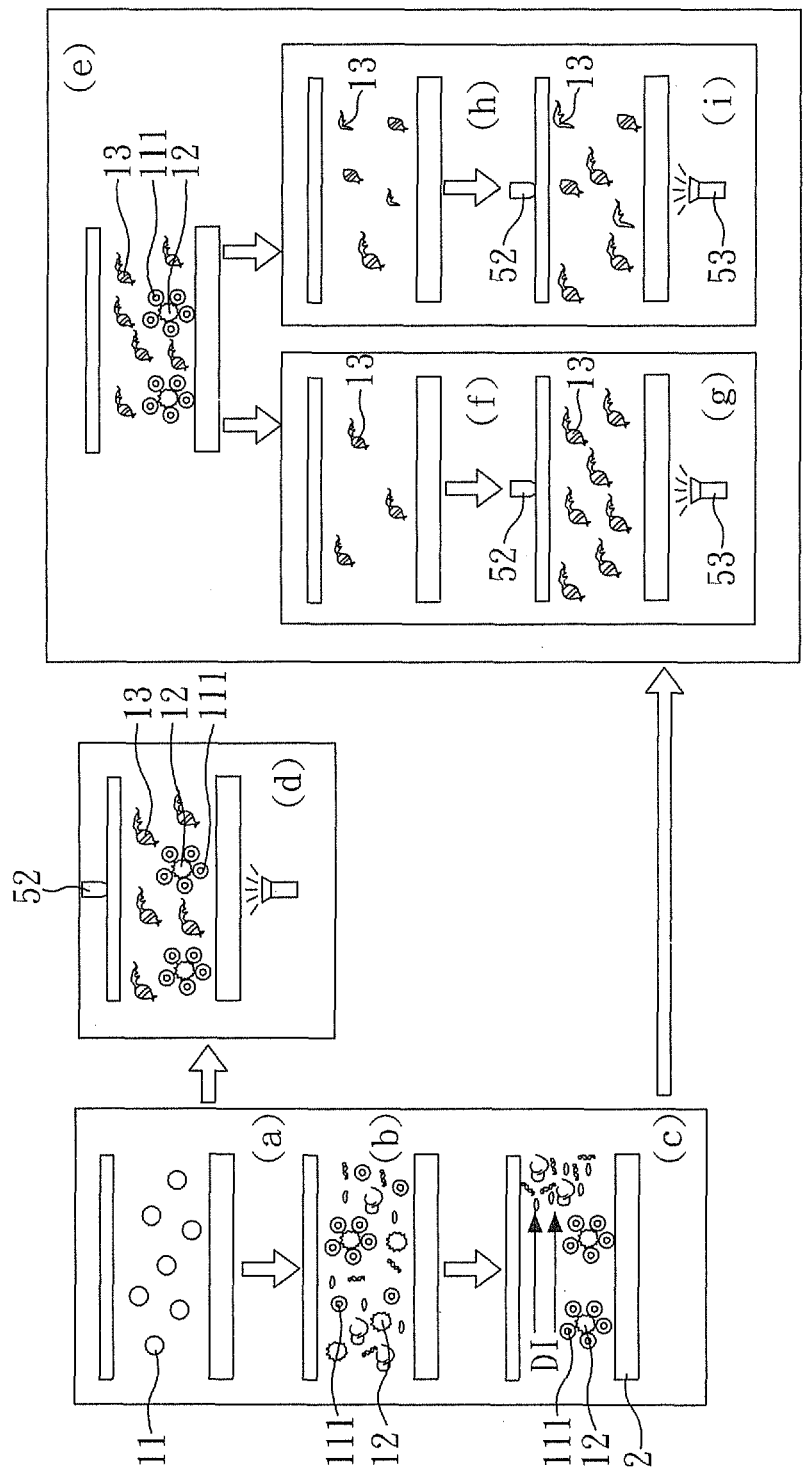
FIG. 1 is a perspective view showing a method for detecting mtDNA alterations according to Embodiment 1 of the present invention.
Figure 2B:
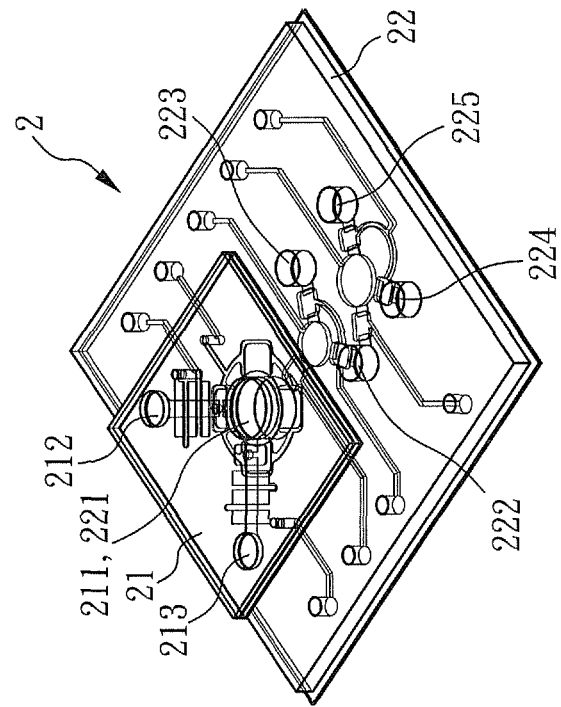
FIG. 2B is a perspective view showing a device for detecting mtDNA alterations according to Embodiment 1 of the present invention.
Figure 2A:
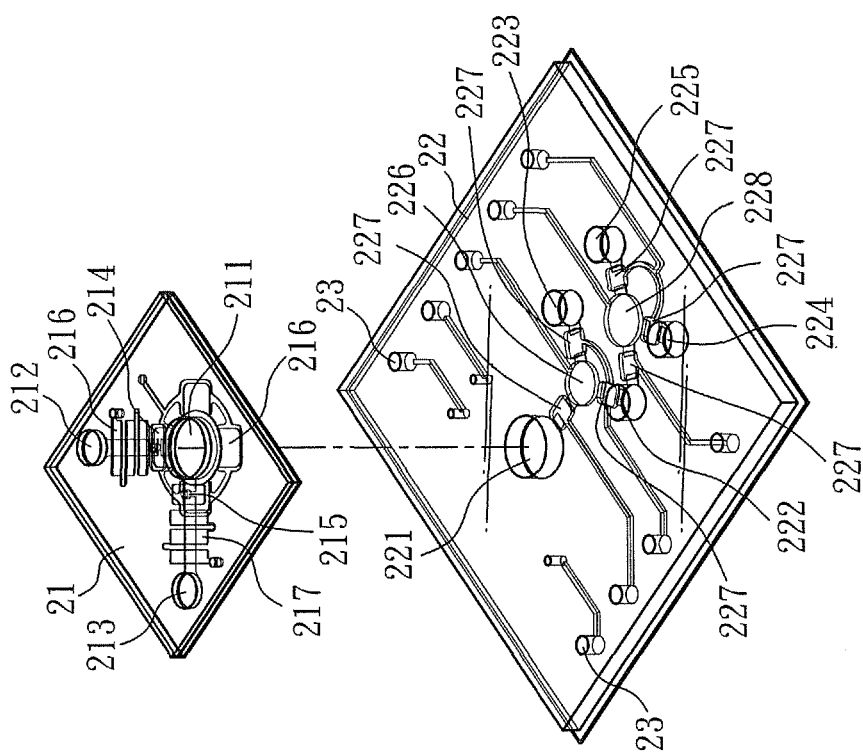
FIG. 2A is a exploded view showing a device for detecting mtDNA alterations according to Embodiment 1 of the present invention.
Figure 3:
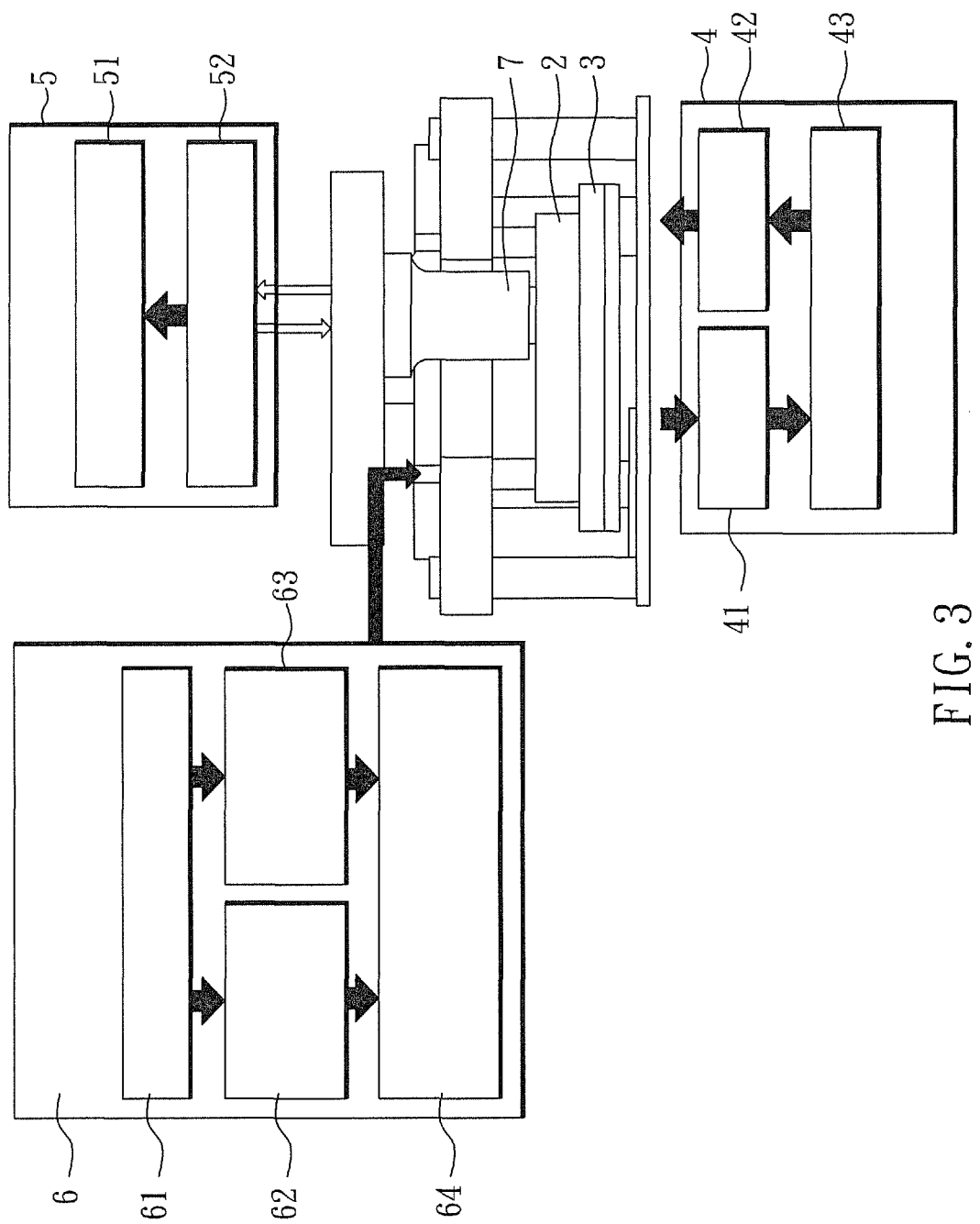
FIG. 3 is a perspective view showing a system detecting mtDNA alterations according to Embodiment 1 of the present invention.

FIG. 1 is a perspective view showing a method for detecting mtDNA alterations of the present embodiment, FIG. 2A and FIG. 2B are respectively a exploded view and a perspective view showing a device for detecting mtDNA alterations of the present embodiment, and FIG. 3 is a perspective view showing a system detecting mtDNA alterations of the present embodiment.

As shown in FIG. 2A and FIG. 2B, the device for detecting mtDNA alterations of the present embodiment comprises: a purification unit 21 containing a first reaction chamber 211 and a separation-element storage chamber 212, wherein the separation-element storage chamber 212 connects to the first reaction chamber 211 through a first pump 214; and a detection unit 22 disposed under the purification unit 21, wherein the detection unit 22 comprises: a second reaction chamber 221 and a detecting-sample chamber 224, the second reaction chamber 221 connects to the first reaction chamber 211, and the detecting-sample chamber 224 connects to the second reaction chamber 221 through a second pump 228. Herein, the first pump 214 is a peristaltic micropump, and the second pump 228 is a suction-type micropump. In addition, a connection path 217 is disposed between the first pump 214 and the separation-element storage chamber 212, and a separation element contained in the separation-element storage chamber 212 is introduced into the separation-element storage chamber 212 by the first pump 214 to react with a sample contained in the first reaction chamber 211.

In addition, in the device for detecting mtDNA alterations of the present embodiment, the purification unit 21 further comprises a washing-solution storage chamber 213, which connects to the first reaction chamber 211 through a third pump 215. In addition, a connection path 217 is disposed between the third pump 215 and the washing-solution storage chamber 213, and a washing solution (such as water) contained in the washing-solution storage chamber 213 is passed through the connection path 217 and introduced into the first reaction chamber 211 by the third pump 215. Herein, the third pump 215 is a peristaltic micropump.

In the device for detecting mtDNA alterations of the present embodiment, the detection unit 22 further comprises: a mitochondria-gene checking chamber 223 and a temporary chamber 222, wherein the mitochondria-gene checking chamber 223 and the temporary chamber 222 connect to the second reaction chamber 221 through a fourth pump 226, and the temporary chamber 222 also connects to the detecting-sample chamber 224 through the second pump 228. Herein, connection paths between the mitochondria-gene checking chamber 223/the temporary chamber 222 and the fourth pump 226 are back pressure paths 227, and the sample contained in the second reaction chamber 221 can be divided equally into the mitochondria-gene checking chamber 223 and the temporary chamber 222. In addition, connection paths between the temporary chamber 222 and the second pump 228 and between the second reaction chamber 221 and the fourth pump 226 are back pressure paths.

Furthermore, in the device for detecting mtDNA alterations of the present embodiment, the detection unit 22 further comprises: a comparison sample chamber 225, which connects to the temporary chamber 222 through the second pump 228. Herein, connection paths between the comparison sample chamber 225/the detecting-sample chamber 224 and the second pump 228 are back pressure paths, and the sample contained in the temporary chamber 222 can be divided equally into the comparison sample chamber 225 and the detecting-sample chamber 224 to perform the sequential detection process.

In addition, in the device for detecting mtDNA alterations of the present embodiment, the detection unit 22 further comprises: plural gas inlets 23, wherein each gas inlets 23 respectively connects to the first pump 214, the second pump 228, the third pump 215, the forth pump 226, the micro-mixture unit 216, the connection path between the second reaction chamber 221 and the fourth pump 226, the connection path between the mitochondria-gene checking chamber 223 and the temporary chamber 222, the connection path between the temporary chamber 222 and the second pump 228, and the connection path between the detecting-sample chamber 224 and the comparison sample chamber 225. Compressed gas can be introduced from the gas inlets 23 to facilitate the sample flowing between each connection path.

Then, as shown in FIG. 3, the system for detecting mtDNA alterations of the present embodiment comprises: the aforementioned device 2 for detecting mtDNA alterations; a temperature controller 4 disposed surrounding the device 2 to control a temperature of the device 2, wherein the temperature controller 4 is disposed under the device 2 in the present embodiment; and an analysis device 5 disposed over the device 2 to detect signals emitting from the sample contained in the device 2. Herein, the system for detecting mtDNA alterations of the present embodiment further comprises a heater/cooler device 3, which is disposed under the device 2 and connects to the temperature controller 4. In the present embodiment, the heater/cooler device 3 is a TE cooler.

In addition, the temperature controller 4 of the present embodiment comprises: a temperature sensing module 41, a power supply 42, and a control module 43. The temperature sensing module 41 can detect the temperature of the device 2. The control module 43 can control the power supply 42 providing power to the heater/cooler device 3 based on the temperature detected by the temperature sensing module 41 to increase or decrease the temperature of the device 2. Herein, the detailed structure of the temperature controller 4 is only one embodiment of the present invention, and the present invention is not limited thereto.

Furthermore, the analysis device 5 of the present invention is a fluorescence device, which comprises: a processor 51 and a photomultiplier tube 52. The photomultiplier tube 52 provides an excitation light to the device 2 and receives signals emitted from the device 2, and the signals received by the photomultiplier tube 52 are outputted by the processor 51. The photomultiplier tube 52 can convert photo signals into electric signals, and amplify the electric signals to obtain the signals emitted from the device 2. Herein, the detailed structure of the analysis device 5 is only one embodiment of the present invention, and the present invention is not limited thereto.

The system for detecting mtDNA alterations of the present embodiment further comprises an electromagnetic controller 6, which provides a magnetic field to the device 2. Herein, the electromagnetic controller 6 comprises: a power supply 61, a vacuum pump 62, a digital controller 63, and a solenoid valve 64. The power supply 61 provides power to the vacuum pump 62 and the digital controller 63, and then signals are transmitted to the solenoid valve 64 to output a magnetic field to the device 2. Herein, the detailed structure of the electromagnetic controller 6 is only one embodiment of the present invention, and the present invention is not limited thereto.

Furthermore, the system for detecting mtDNA alterations of the present embodiment further comprises an object lens 7. The excitation light emitted from the analysis device 5 can be focused on a detection region by the object lens 7, and then the object lens 7 can receive signals emitted from the excited sample to improve the detection effect of the analysis device 5.

Hereafter, the device, the system and the method for detecting mtDNA alterations of the present embodiment are explained accompanied with FIG. 1 to FIG. 3 of the present invention.

First, as shown in FIG. 1, FIG. 2A and FIG. 3, a sample 11 (i.e. cells) contained with mitochondria genes is provided in the first reaction chamber 211 (as shown in FIG. 1(a)), and a separation element 12 (such as magnetic beads) is provided in the separation-element disposed chamber 212 of the device 2. After the sample 11 is lysed, the separation element 12 contained in the separation-element disposed chamber 212 is introduced into the first reaction chamber 211 through the first pump 214 (as shown in FIG. 1(b)), and then the sample 11 is well mixed with the separation element 12 by the micro-mixture unit 216. Mitochondria genes 111 can bind to the separation element 12 via a DNA fragment for recognizing mitochondria genes modified on the separation element 12. The electromagnetic controller 6 provides a magnetic field to the device 2 to separate the mitochondria genes 111 from other matrix of the cells. Then, a washing solution contained in the washing-solution storage chamber 213 is introduced into the washing-solution storage chamber 213 to remove other matrix of the cells (as shown in FIG. 1(c)) to obtain a detecting sample.

Next, as shown in FIG. 1, FIG. 2B and FIG. 3, the first reaction chamber 211 and the second reaction chamber 221 together form a reaction chamber, the fourth pump 226 can introduce the detecting sample contained in the second reaction chamber 221 into the mitochondria-gene checking chamber 223 and the temporary chamber 222, and the detecting sample is divided into a mitochondria gene-checking group and a detecting sample part (as shown in FIG. 1(d) and (e)). Then, an amplification solution is added into the mitochondria-gene checking chamber 223 to identify whether the mitochondria genes are present or not. This step is a checking step of an extraction process on mitochondria gene. The amplification solution comprises a labeling reagent and a primer pair. The labeling reagent can be any DNA labeling reagent generally used in the art, and the sequence of the primer pair can be any sequence selected from the mitochondria gene. In the present embodiment, the labeling reagent is a reagent which can chelate into major grooves of DNAs to emit fluorescence, and the sequence of the primer pair contains a sequence that can pair with a D-loop region of the mitochondria genes. After a PCR or a real-time PCR is performed together with a heater/cooler device 3 to amplify DNAs, that is, to form amplimers 13, which are contained in the detecting sample, a light source 53 provides light on the detecting sample, and whether the mitochondria genes are present in the mitochondria gene-checking group of the detecting sample or not is determined by the photomultiplier tube 52 of the analysis device (as shown in FIG. 1(d)).

As shown in FIG. 1, FIG. 2A and FIG. 3, when it is confirmed that the mitochondria genes are indeed present in the mitochondria gene-checking group of the detecting sample, the detecting sample group of the detecting sample contained in the temporary chamber 222 is divided into a comparison group (as shown in FIG. 1(f)) in the comparison sample chamber 225 and a detection group (as shown in FIG. 1(h)) in the detecting-sample chamber 224 by the second pump 228 to perform a detection process. An amplification solution is added into the comparison group in the comparison sample chamber 225 and the detection group in the detecting-sample chamber 224 respectively, a restriction enzyme is also added into the detection group in the detecting-sample chamber 224, and then a DNA amplified reaction is performed. The amplification solution comprises a labeling reagent and a primer pair. The labeling reagent can be any DNA labeling reagent generally used in the art, and the sequence of the primer pair can be a target gene region selected from the mitochondria genes. In the present embodiment, the labeling reagent is a reagent which can chelate into major grooves of DNAs to emit fluorescence, the sequence of the primer pair contains a sequence that can pair with a target gene region selected from the mitochondria genes, and the restriction enzyme is an enzyme capable of digesting DNAs in the target gene of the mitochondria genes. It should be noted that the primer pair added into the comparison group is the same as that added into the detection group. After a PCR or a real-time PCR is performed together with a heater/cooler device 3 to amplify DNAs contained in the detecting sample, the light source 53 provides light on the detecting sample, and whether the mitochondria genes in the detecting sample are mutated or not is determined by the photomultiplier tube 52 of the analysis device (as shown in FIG. 1(g) and (i)). When the amount of the labeling reagent in the detection group is less than that in the comparison group by analyzing with the analysis device 5, it indicates that a mitochondria mutation is present in the sample.

EXAMPLE 1

The device, the system and the method for detecting mtDNA alterations according to Embodiment 1 are used in the present example. The device, the system and the method used in the present example are the same as those in Embodiment 1, so the detailed description is omitted herein.

Mutated Mitochondria Gene (mtDNA) Group

Magnetic beads (1.08 μm, Dynabeads® MyOne™ Carboxylic Acid, Invetrogen, USA) surface-immobilized with specific DNA fragments were used, wherein the sequence of the DNA fragments was TGGTATTTTCGTCTGGGGGG-TATG (SEQ ID NO: 1); the washing solution was de-ionized water (DI); the cell lines were Lu03 (cell lines with A3243G point-mutated mtDNA); the primer pair of the amplification solution added into the mitochondria-gene checking chamber had sequences shown in the following Table 1 (as shown in SEQ ID NOs: 4 and 5); the used restriction enzyme is ApaI, which can digest the sequence with A3243G point-mutated mtDNA but not digest normal mtDNA without mutations); the DNA amplified reaction was a PCR; the analysis device comprised a PMT system (C3830, R928; Hamamatsu Photonics, Japan); eight electromagnetic valves (EMVs; S070M-5BG-32, SMC, Japan) were used; the heater/cooler device was a TE cooler, wherein the working temperatures were set 60° C. for cell lysis, 37° C. for enzyme digestion and 95° C., 58° C. and 72° C. for PCR amplification; the labelling reagent was a fluorescent reagent contained in KAPA SYBR® FAST qPCR kits (KK4603, Kapa Biosystems, MA, USA); and the target region of the mitochondria genes was A3243G.

Normal mtDNA Group

The conditions of this group were the same as those in the mutated mtDNA group, except that the cell lines were Lu02 (cell lines with normal mtDNA).

TABLE 1

| | Target region of mtDNA/ Annealing temperature | Primers (5'→3') |
|---|---|---|
| Checking step of an extraction process on mtDNA | L3085-H3415 (332 bps)/ 58° C. | L3085: taatccaggtcg gtttct (SEQ ID NO: 2) H3415: tatgttgatgcg tttccg (SEQ ID NO: 3) |
| Detection process | L5604-H5863 (279 bps)/ 58° C. | L5604: cactctgcatca actgaacg (SEQ ID NO: 4) H5863: agtccaatgctt cactcagc (SEQ ID NO: 5) |

Figure 4:
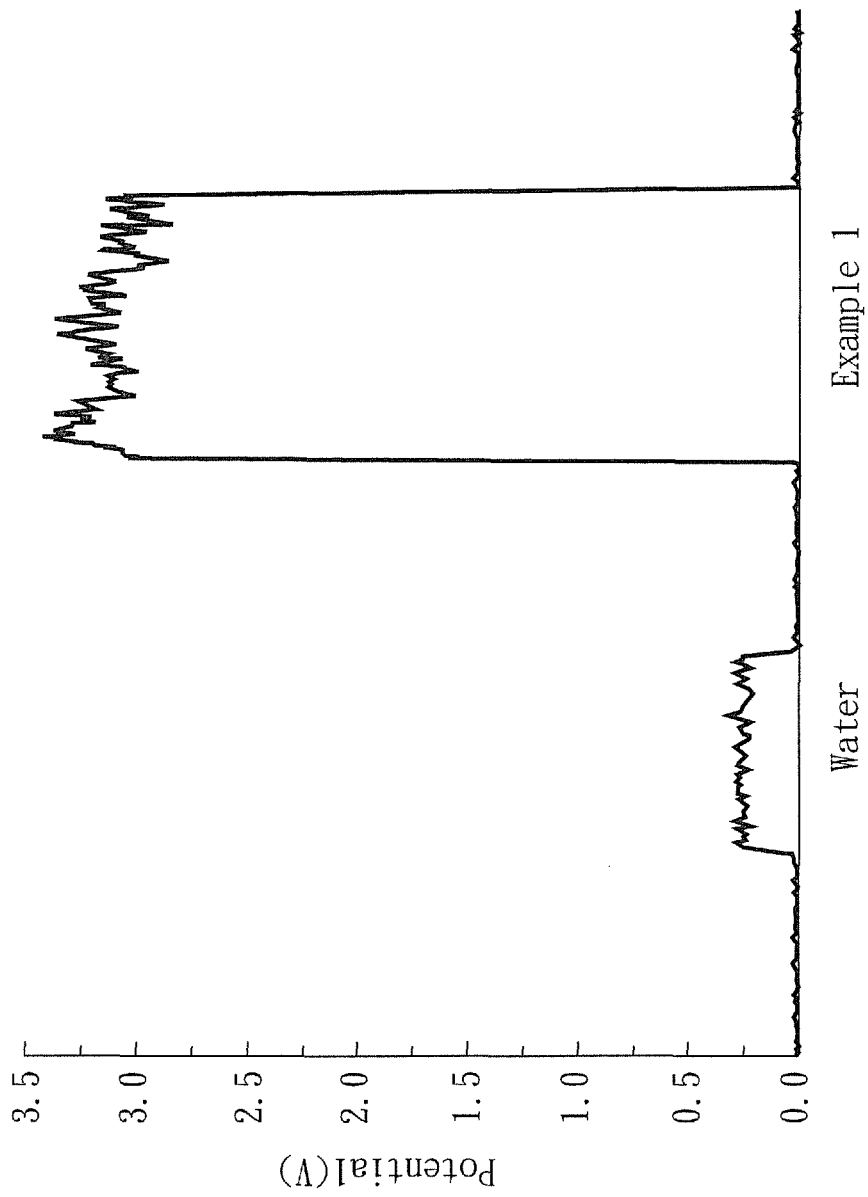
FIG. 4 is a result of a checking step of an extraction process on mitochondria genes according to Example 1 of the present invention.

FIG. 4 is a result of a checking process of an extraction process on mtDNA (i.e. the step shown in FIG. 1(d)). This result indicates that the mtDNA indeed can be extracted from the sample and the PMT system can detect the signals of the fluorescent reagent labeled on the mtDNA, when the system of Embodiment 1 was used. Conversely, if the sample was water and did not contain mtDNA, the PMT system almost cannot detect any signals.

Figure 5:
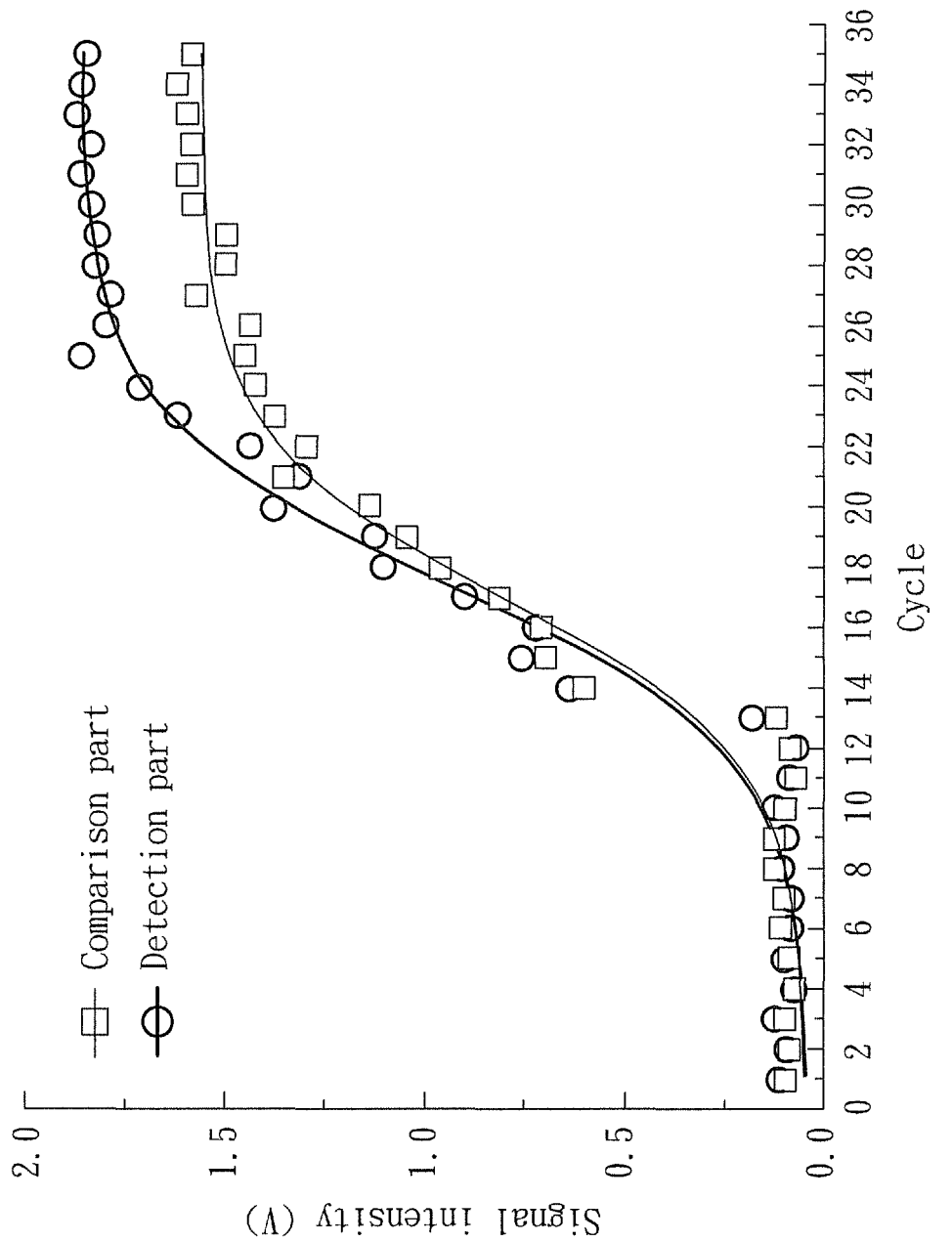
FIG. 5 is a detecting result of normal mtDNA group according to Example 1 of the present invention.
Figure 6:
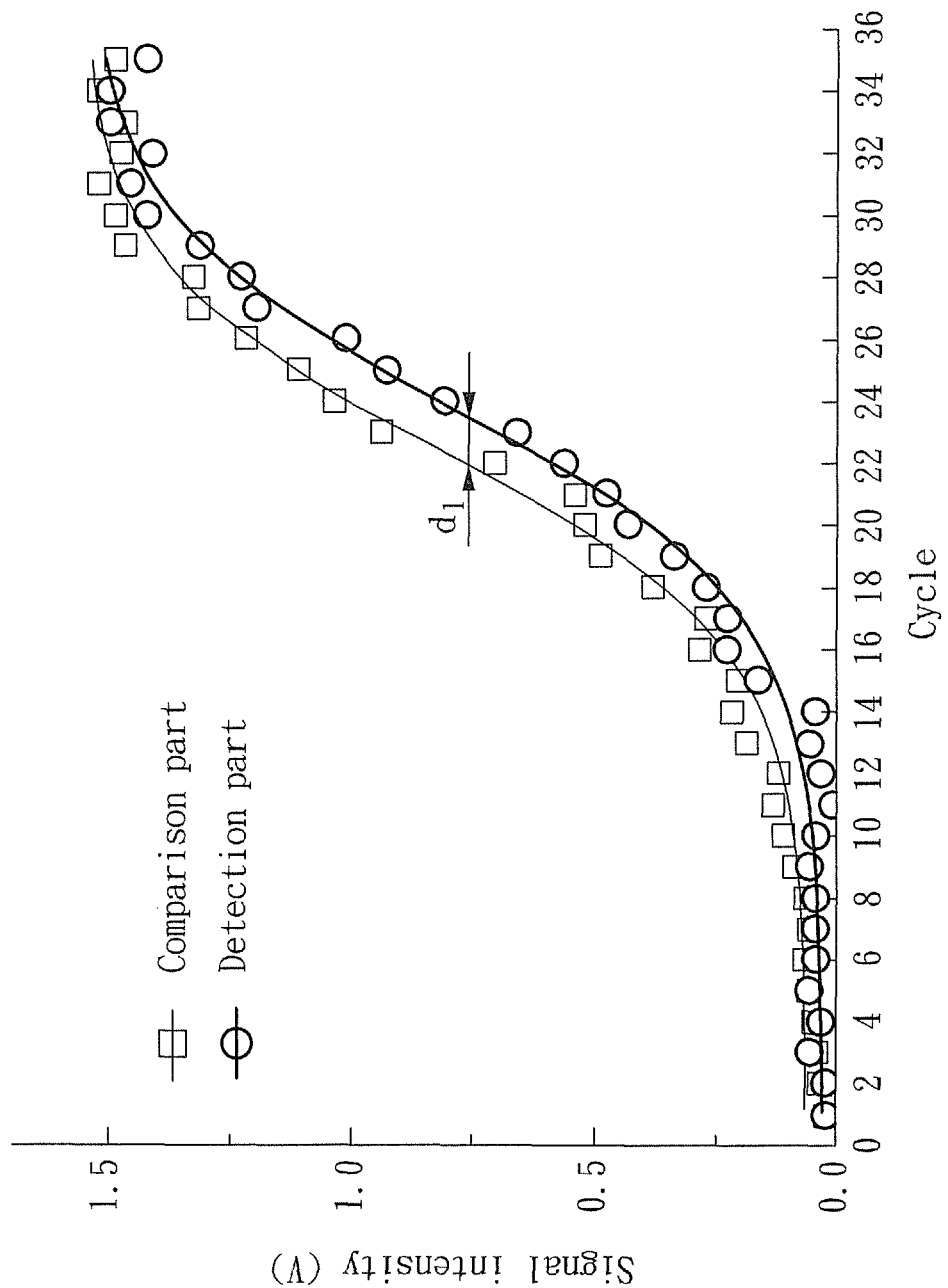
FIG. 6 is a detecting result of mutated mtDNA group according to Example 1 of the present invention.

FIG. 5 and FIG. 6 are detection results of normal mtDNA group and mutated mtDNA group according to the present example. As shown in FIG. 5, the used ApaI cannot recognize mtDNA without mutations (i.e. normal mtDNA), so no fluorescent signal shift was found between the detection group in the detecting-sample chamber and the comparison group in the comparison sample chamber after several cycles of DNA amplifications. However, as shown in FIG. 6, the used ApaI can recognize and digest point-mutated mtDNA, so there a fluorescent signal shift $d_1$ was found between the detection group in the detecting-sample chamber and the comparison group in the comparison sample chamber after several cycles of DNA amplifications.

COMPARATIVE EXAMPLE 1

The purpose of the present comparative example is to confirm that the method, the device and the system for detecting mtDNA alterations of Embodiment 1 can accomplish similar effect as those generally used in the art. In the present comparative example, a conventional real-time PCR machine was used, in which the reaction temperature, the sample, the sequences of the primer pair including the mutated mtDNA group and the normal mtDNA group, and the restriction enzyme were the same as those used in Example 1. The results are shown in FIG. 7 and FIG. 8.

Figure 7:
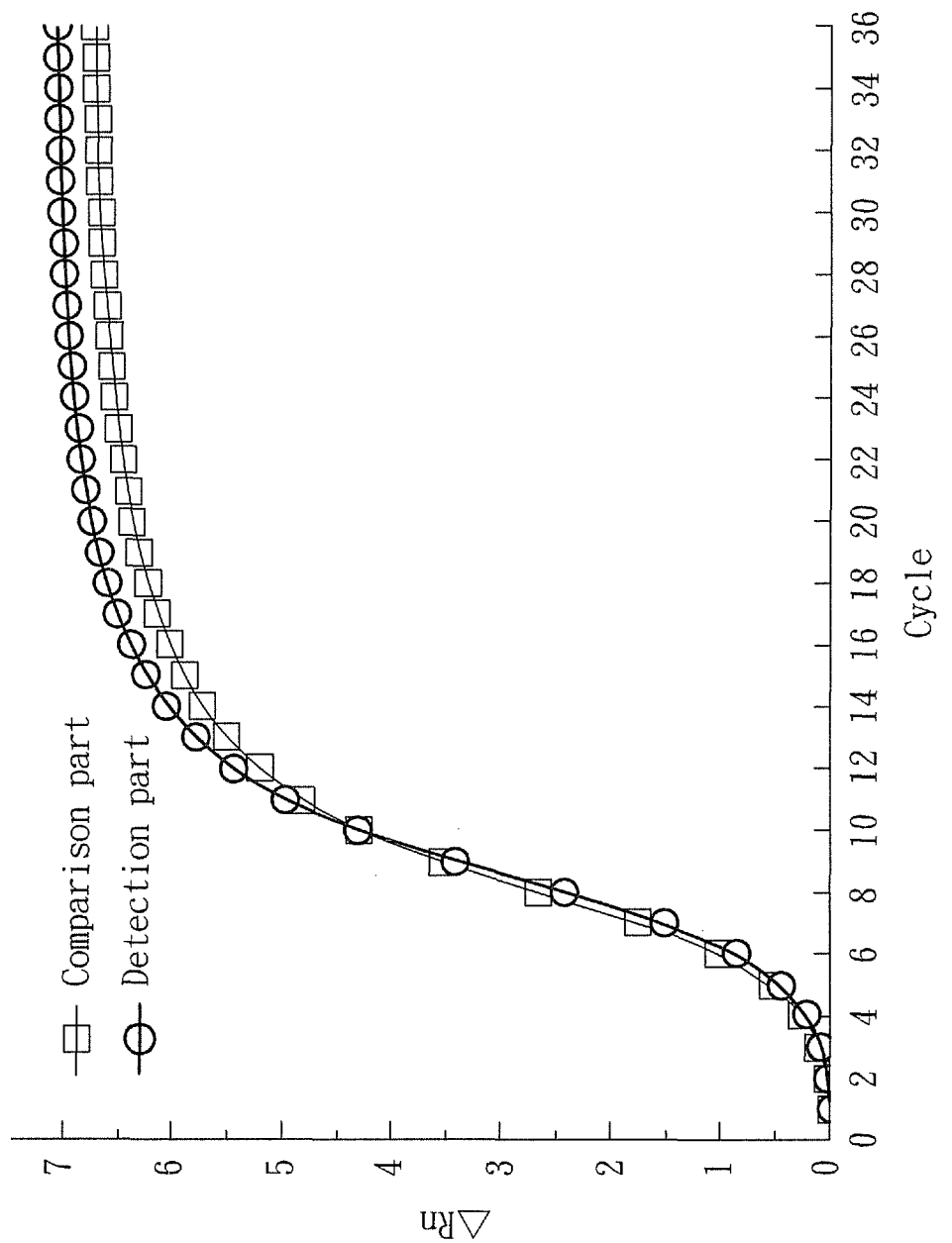
FIG. 7 is a detecting result of normal mtDNA group according to Comparative Example 1 of the present invention.
Figure 8:
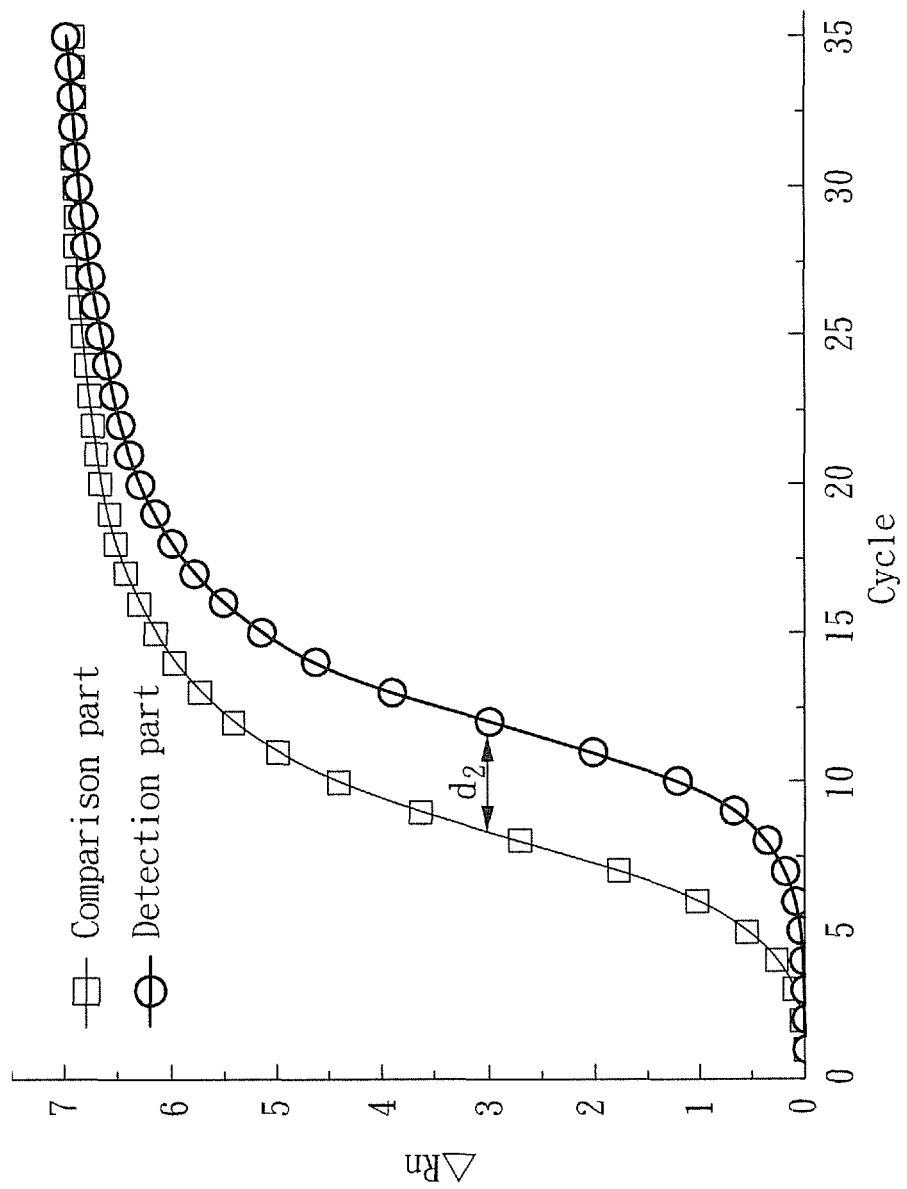
FIG. 8 is a detecting result of mutated mtDNA group according to Comparative Embodiment 1 of the present invention.

As show in FIG. 7, the used ApaI cannot recognize mtDNA without mutations (i.e. normal mtDNA), so no fluorescent signal shift was found between the comparison group in the comparison sample chamber (without adding the restriction enzyme) and the detection group in the detecting-sample chamber (with adding the restriction enzyme) after several cycles of DNA amplifications. However, as shown in FIG. 8, the used ApaI can recognize and digest point-mutated mtDNA, so in that case a fluorescent signal shift $d_2$ was found between the comparison group in the comparison sample chamber and the detection group in the detecting-sample chamber after several cycles of DNA amplifications. $\Delta$ Rn in the figure shows the significant fluorescent signals detected by the analysis device.

EXAMPLE 2

The device, the system and the method for detecting mtDNA alterations according to Embodiment 1 were used in the present example to detect mtDNA with 0, 30, 60, 90, 100% mutation degree. The mutation degree means the ratio of mutated mtDNA in total amount of extracted mtDNA in the sample.

COMPARATIVE EXAMPLE 2

The real-time PCR machine of Comparative Example 1 was used in the present comparative example to detect mtDNA with 0, 30, 60, 90, 100% mutation degree.

Figure 9:
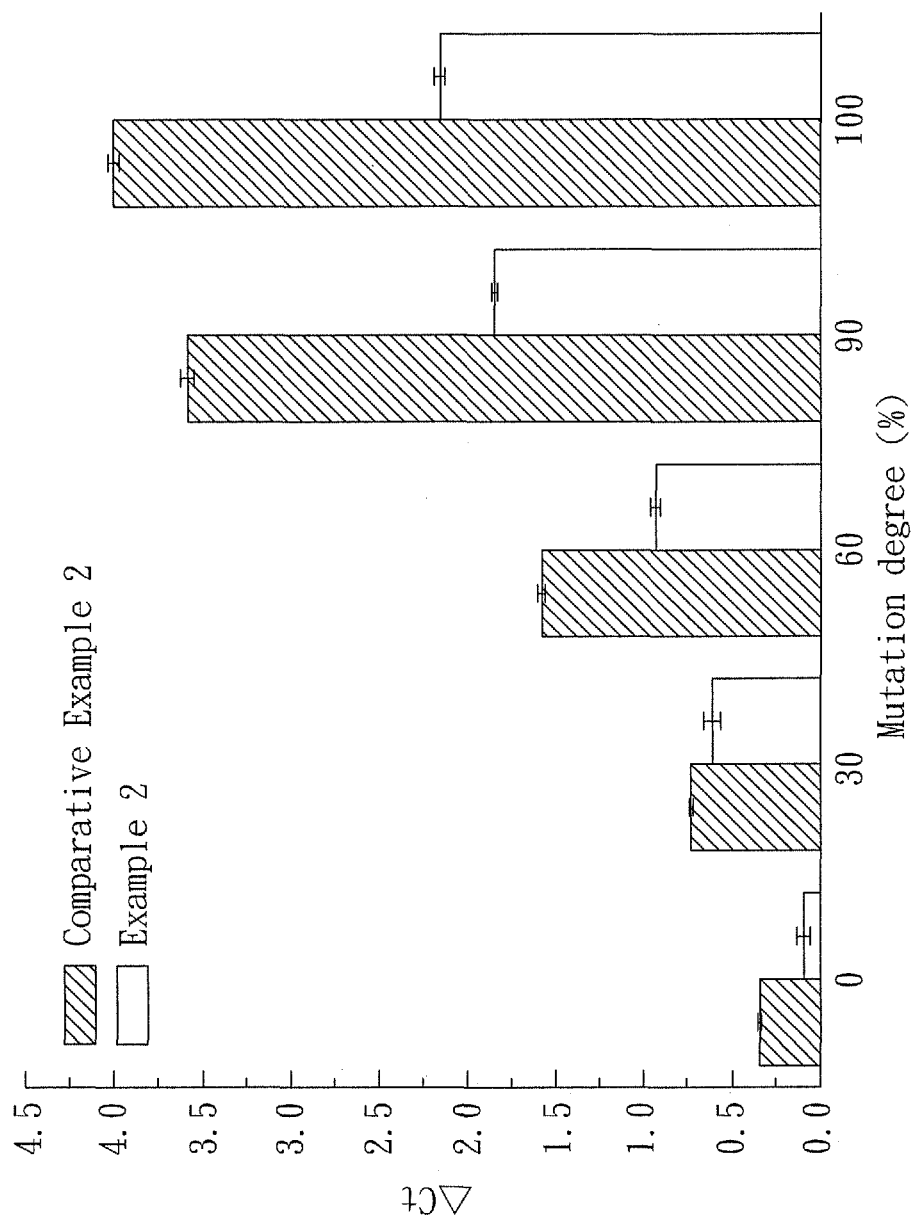
FIG. 9 is a detecting result according to Example 2 and Comparative Example 2 of the present invention.

As shown in FIG. 9, the mutation degree is directly proportional to the detected signals. The result detected by the device, the system and the method for detecting mtDNA alterations according to Embodiment 1 and that detected by the conventional real-time PCR machine are similar. $\Delta$ Ct is a differential value from the increasing curve of PCR detected in the comparison sample chamber and the detecting-sample chamber in each cycle.

The results of Examples 1-2 and Comparative Examples 1-2 will show that the method, the device and the system for detection mtDNA alterations of Embodiment 1 can incur similar effect to the conventional device.

In conclusion, the method, the device and the system for detection mtDNA alterations of the present invention indeed can work to detect mtDNA alterations. More particularly, the device provided by the present invention can perform cell lysis, enzyme digestion and optical detection on a single device, so that complex treatment and detection can be simplified. In addition, the device of the present invention is a cheap, micro-sized and disposable device, so detection on mtDNA alterations can be performed rapidly and easily accessible to the public. Hence, the device of the present invention can further be applied in clinical settings to determine whether a subject is at risk of contracting diseases related to mitochondria gene alterations.

Although the present invention has been explained in relation to its preferred embodiment, it is to be understood that many other possible modifications and variations can be made without departing from the spirit and scope of the invention as hereinafter claimed.

What is claimed is:

1. A method for detecting mitochondria gene alterations in a microfluidic device, comprising the following steps:
   (A) providing a microfluidic device, comprising:
      (i) a purification unit comprising a first reaction chamber and a separation element storage chamber, wherein the separation element storage chamber connects to the first reaction chamber through a first pump, the separation element storage chamber comprises a separation element, and the separation element is modified with a DNA fragment capable of recognizing mitochondrial genes; and
      (ii) a detection unit disposed under the purification unit, wherein the detection unit comprises a second reaction chamber, a detecting sample chamber, and a comparison chamber, the second reaction chamber connects to the first reaction chamber, and the detecting sample chamber and the comparison chamber connect to the second reaction chamber through a second pump;
   (B) providing a sample containing mitochondria genes;
   (C) placing the sample into the first reaction chamber, and introducing the separation element into the first reaction chamber using the first pump, to separate the mitochondria genes from the sample through a binding between the DNA fragment of the separation element and the mitochondria genes in the sample, so as to obtain a detecting sample containing the mitochondria genes;
   (D) introducing a first portion of the detecting sample into the detecting sample chamber and a second portion of the detecting sample into the comparison chamber using the second pump;
   (E) adding an amplification solution into both the detecting sample chamber and the comparison chamber and further adding a restriction enzyme into the detecting sample chamber, wherein the amplification solution comprises a labeling reagent and a primer pair, and the restriction enzyme includes ApaI for digesting a target gene region of the mitochondria genes;
   (F) performing a DNA amplified reaction in both the detecting sample chamber and the comparison chamber, wherein the primer pair is used to amplify the target gene region of the mitochondria genes;
   (G) determining the relative amount of amplified DNA by measuring a signal from the labeling reagent in the detecting sample chamber and the comparison chamber; and
   (H) comparing the difference between the signals of the detecting sample chamber and the comparison chamber;
   wherein when the amount of signal in the detecting sample chamber is less than that in the comparison chamber, it indicates that a mitochondria gene alteration is present in the sample.

2. The method of claim 1, wherein step (D) further comprises obtaining a third portion of the detecting sample and confirming that mitochondria genes are present in the detecting sample by detecting mitochondria genes in the third portion.

3. The method of claim 2, wherein the mitochondria genes are detected through a polymerase chain reaction (PCR) or a real-time polymerase chain reaction (real-time PCR).

4. The method of claim 3, wherein a primer pair used in the PCR or the real-time PCR pairs with a D-loop region of the mitochondria genes.

5. The method of claim 1, wherein the labeling reagent used in step (E) is a fluorescent dye.

6. The method of claim 1, wherein the DNA amplified reaction used in step (F) is a PCR or a real-time PCR.

7. The method of claim 1, wherein the separation element is a magnetic bead or a polymer bead.

* * * * *